(12) United States Patent
Hyltander et al.

(10) Patent No.: US 9,153,146 B2
(45) Date of Patent: Oct. 6, 2015

(54) METHOD AND SYSTEM FOR SIMULATION OF SURGICAL PROCEDURES

(75) Inventors: Anders Hyltander, Askim (SE); Anders Larsson, Kode (SE); David Löfstrand, Göteborg (SE); Hans Lönroth, Kullavik (SE)

(73) Assignee: SURGICAL SCIENCE SWEDEN AB, Gothenburg (SE)

( * ) Notice: Subject to any disclaimer, the term of this patent is extended or adjusted under 35 U.S.C. 154(b) by 1713 days.

(21) Appl. No.: 10/466,524

(22) Filed: Jul. 17, 2003

(65) Prior Publication Data
US 2006/0073454 A1 Apr. 6, 2006

(30) Foreign Application Priority Data

Jan. 24, 2001 (SE) .................................... 0100184-1

(51) Int. Cl.
| G09B 23/28 | (2006.01) |
| A61B 19/00 | (2006.01) |
| G06T 19/00 | (2011.01) |
| G06T 19/20 | (2011.01) |
| G09B 19/00 | (2006.01) |

(Continued)

(52) U.S. Cl.
CPC ............. *G09B 23/285* (2013.01); *A61B 19/50* (2013.01); *G06T 19/00* (2013.01); *G06T 19/003* (2013.01); *G06T 19/20* (2013.01); *G09B 23/288* (2013.01); *A61B 19/5244* (2013.01); *A61B 2017/00707* (2013.01); *G06F 19/3437* (2013.01); *G06T 2207/10136* (2013.01); *G06T 2207/30004* (2013.01); *G09B 19/00* (2013.01)

(58) Field of Classification Search
CPC .. G09B 19/00; G09B 19/3437; G09B 23/288; G06F 19/3437; A61B 19/50; A61B 19/5244; A61B 2017/00707; G06T 19/00; G06T 19/003; G06T 19/20; G06T 2207/10136; G06T 2207/30004
USPC ......................................... 434/262, 267, 272
See application file for complete search history.

(56) References Cited

U.S. PATENT DOCUMENTS

| 4,464,123 A | * | 8/1984 | Glover et al. ................. 434/268 |
| 4,907,973 A | * | 3/1990 | Hon .............................. 434/262 |
| 5,296,379 A | * | 3/1994 | Gorog et al. .................... 436/69 |

(Continued)

FOREIGN PATENT DOCUMENTS

| JP | 10111958 | 4/1998 |
| JP | 11-161813 | 6/1999 |

(Continued)

*Primary Examiner* — Nikolai A Gishnock
(74) *Attorney, Agent, or Firm* — Harness, Dickey & Pierce, P.L.C.

(57) ABSTRACT

A method and a system are for simulating a surgical procedure on a bodily object, such as an organ, in a virtual environment. The virtual environment includes a three-dimensional mathematically described model of the bodily object which reflects geometrical and mechanical properties, and a virtual instrument that is controlled by a physical feeding device, which makes it possible to affect the model. The method includes the steps of representing a two-dimensional projection of the model by way of a video sequence containing a recorded view of a real bodily object, wherein engagement with the virtual instrument only involves interacting with the model. In addition, a method is for simulating an operation containing several surgical procedures.

4 Claims, 3 Drawing Sheets

(51) Int. Cl.
  *G06F 19/00* (2011.01)
  *A61B 17/00* (2006.01)

(56) References Cited

U.S. PATENT DOCUMENTS

| | | | | |
|---|---|---|---|---|
| 5,584,701 A * | 12/1996 | Lampotang et al. | ........... | 434/272 |
| 5,609,485 A * | 3/1997 | Bergman et al. | .............. | 434/262 |
| 5,769,640 A | 6/1998 | Jacobus et al. | | |
| 5,769,641 A * | 6/1998 | Lampotang et al. | ........... | 434/272 |
| 5,772,442 A * | 6/1998 | Lampotang et al. | ........... | 434/265 |
| 5,772,443 A * | 6/1998 | Lampotang et al. | ........... | 434/272 |
| 5,779,484 A * | 7/1998 | Lampotang et al. | ........... | 434/266 |
| 5,791,907 A | 8/1998 | Ramshaw et al. | | |
| 5,800,179 A * | 9/1998 | Bailey | ........................... | 434/262 |
| 5,821,920 A * | 10/1998 | Rosenberg et al. | ........... | 345/156 |
| 5,823,787 A * | 10/1998 | Gonzalez et al. | ............. | 434/265 |
| 5,868,579 A * | 2/1999 | Lampotang et al. | ........... | 434/262 |
| 5,882,206 A * | 3/1999 | Gillio | ........................... | 434/262 |
| 5,882,207 A * | 3/1999 | Lampotang et al. | ........... | 434/268 |
| 5,890,908 A * | 4/1999 | Lampotang et al. | ........... | 434/268 |
| 5,909,380 A * | 6/1999 | Dubois et al. | .................. | 703/11 |
| 5,941,710 A * | 8/1999 | Lampotang et al. | ........... | 434/272 |
| 5,945,056 A * | 8/1999 | Day et al. | ...................... | 264/250 |
| 5,947,744 A * | 9/1999 | Izzat | ............................... | 434/272 |
| 6,061,462 A * | 5/2000 | Tostevin et al. | ............... | 382/100 |
| 6,074,213 A * | 6/2000 | Hon | ............................... | 434/262 |
| 6,106,301 A * | 8/2000 | Merril | ........................... | 434/262 |
| 6,151,009 A * | 11/2000 | Kanade et al. | ................. | 345/641 |
| 6,215,470 B1 * | 4/2001 | Rosenberg et al. | ........... | 345/156 |
| 6,234,804 B1 * | 5/2001 | Yong | ............................. | 434/267 |
| 6,331,116 B1 * | 12/2001 | Kaufman et al. | .............. | 434/262 |
| 6,395,016 B1 * | 5/2002 | Oron et al. | ........................ | 607/88 |
| 6,443,974 B1 * | 9/2002 | Oron et al. | ........................ | 607/88 |
| 6,450,978 B1 * | 9/2002 | Brosseau et al. | .............. | 600/595 |
| 6,468,265 B1 * | 10/2002 | Evans et al. | ......................... | 606/1 |
| 6,533,737 B1 * | 3/2003 | Brosseau et al. | .............. | 600/595 |
| 6,544,041 B1 * | 4/2003 | Damadian | ..................... | 434/262 |
| 6,575,751 B1 * | 6/2003 | Lehmann et al. | .............. | 433/223 |
| 6,605,053 B1 * | 8/2003 | Kamm et al. | ..................... | 604/8 |
| 6,659,939 B2 * | 12/2003 | Moll et al. | .................... | 600/102 |
| 6,929,481 B1 * | 8/2005 | Alexander et al. | ........... | 434/262 |
| 7,191,110 B1 * | 3/2007 | Charbel et al. | .................. | 703/11 |
| 2001/0019818 A1* | 9/2001 | Yong | ............................. | 434/262 |

FOREIGN PATENT DOCUMENTS

| | | |
|---|---|---|
| JP | 11175767 | 7/1999 |
| JP | 11219100 | 8/1999 |
| WO | WO 99/17265 | 4/1999 |
| WO | WO 9938141 A1 * | 7/1999 |
| WO | WO 99/42978 | 8/1999 |

* cited by examiner

METHOD AND SYSTEM FOR SIMULATION OF SURGICAL PROCEDURES

This application is the national phase under 35 U.S.C. §371 of PCT International Application No. PCT/SE02/00054 which has an International filing date of Jan. 15, 2002, which designated the United States of America, and which claims priority on Swedish Patent Application No. SE 0100184-1 filed Jan. 24, 2001, the entire contents of which are hereby incorporated by reference.

FIELD OF THE INVENTION

The present invention generally relates to simulation of surgical procedures and, in particular, to simulation of minimal invasive surgical procedures in a virtual environment.

BACKGROUND ART

In modern surgery minimal invasive techniques are used in more and more applications. The development of technology within this relatively new field advances quickly, which results in great training requirements for surgeons. One way of rendering the training more effective is to use computer simulations. Known techniques of providing a credible simulation are very complicated and expensive with respect to computer utility in the form of processor and memory. Moreover, the result is not sufficient to provide a realistic simulation environment. The visual properties that the anatomy exhibits in reality are difficult and time-consuming to recreate in a simulation.

Within the field of laparoscopy a camera is used to supply picture information from the patient to the surgeon. The display screen shows the picture that the camera catches of the inside of, for example, the abdominal cavity. All the instruments and the anatomy with which the surgeon works are reproduced by way of the camera and the display screen. The surgeon uses the information on the display screen to control and operate his or her instruments and carry out the procedures which are required to perform the surgical operation. Since the minimal invasive techniques supply information to the surgeon via a display screen, the three-dimensional reality is reduced to two dimensions on the display screen. The picture therefore lacks, among other things, the information as to depth that exists in reality. The surgeon has to make up for this loss of information by studying lighting conditions, colours, etc.

By use of modern computer engineering, it is possible to provide realistic training situations in a virtual environment created by a computer program. In the computer program, a three-dimensional model of the object which the simulation concerns is provided. The user is provided with a projection thereof which should correspond to the picture information which in a real situation is caught by a camera. Thus, all visual information, such as instrument and anatomy, is drawn by the computer. However, there are still considerable differences between the picture information that the computer tries to recreate and the actual picture that a camera catches. A large part of the picture information that the surgeon uses in real life, for example light effects and anatomic structures, factors such as breathing and beat of the pulse, which are present in the real situation are difficult to recreate realistically in the computer.

Many complicated processes within the field of surgery are expensive, if not impossible, to fully simulate in a computer. This indicates that the simulation can only consist of short procedures which lack the continuity that is usually present when the process is carried out. For instance, in U.S. Pat. No. 5,791,907, Ramshaw et al disclose a system for simulation of an entire operation. This solution is founded on a database of recorded video sequences which visualise different procedures in an operation. The actual simulation then includes the user being introduced to a video sequence which shows a separate procedure. Subsequently, the user is asked a number of questions. Then a video sequence is played showing the continuation of the operation which is determined by the answers to the questions.

SUMMARY OF THE INVENTION

An object of an embodiment of the present invention is to provide a method and a system which create a realistic simulation environment, and which wholly or partly solve the above-mentioned problems. A further object is to provide a method and a system for a realistic simulation of a complete operation.

An embodiment of the present invention relates to a method for simulating a surgical procedure on a bodily object, such as an organ, in a virtual environment provided by a computer unit. The environment comprises a three-dimensional mathematically described model of the bodily object, which reflects at least the geometrical and mechanical properties of the bodily object, and a virtual instrument which is controlled by a physical input device connected to the processing unit, which makes it possible to affect the model. The method according to an embodiment of the invention includes the step of representing a two-dimensional projection of the model by way of a video sequence containing a recorded view of a real bodily object, engagement with the virtual instrument only interacting with the model.

In a virtual environment, an object can be viewed from different angles, but limits are often introduced in order to resemble the real environment. For example, in an operation in the abdomen, limits can be introduced so that a user in the virtual environment can work only from the directions which are physically possible in a real situation. In minimal invasive operations a laparoscopic camera is used to film inside the body. This results in the user limiting himself or herself to one or more viewing angles. Consequently, the virtual environment, i.e. a viewing angle, is determined and by way of this angle a two-dimensional projection is created from the three-dimensional model. This two-dimensional projection corresponds to that shown when a laparoscopic camera is filming inside a body. A bodily object here refers to something in the body that is subjected to the surgical procedure, for example, an organ such as the liver, the heart etc. or, for instance, a cancerous tumour. The computer unit can consist of a computer with associated equipment, for example a personal computer.

The virtual instruments used are controlled by a physical input device. The input device may include, for example, instruments which resemble those used in a real operation, may be mounted in a stand fitted with sensors. One example of such a physical input device is a "Laparoscopic Impulse Engine" which is made by Immersion Corporation, USA. This allows five degrees of freedom, i.e. rotation about a pivoting point (the point where the instrument is inserted into the body), the possibility of moving the instrument longitudinally inwards and outwards, rotation round the axis of the instrument and a gripping function. In order to allow the user to interact with the virtual object and show where the instrument is positioned relative to the same, also the virtual instruments are shown on the display screen. Conveniently, the initial position of the virtual instruments on the display screen is determined by the processing unit; subsequently, they are moved in the virtual environment based on the movements with the input device.

Since the viewing angle for the virtual object is fixed, the two-dimensional projection essentially becomes the same, notwithstanding movements due to pulse, breathing or intervention. If surface rendering is created with the purpose of obtaining a real appearance of the modelled object, it will be possible to simulate an operation. As mentioned by way of introduction, this does not, however, result in a realistic environment. Thus, the method according to an embodiment of the invention uses a recorded video sequence.

The method according to an embodiment of the invention provides a realistic simulation environment which shows the natural movements of an object, such as breathing and pulse. By replacing a computer-created projection of a three-dimensional model of a bodily object with a recorded video sequence, a considerably higher degree of realism is achieved.

A fundamental idea behind an embodiment of the invention is that bodily organs in different human beings essentially have the same structure. However, the computer-based model of the organ essentially has to be similar to the organ in the film. Unlike other solutions, an embodiment of the invention is based on the similarities of organs, i.e. the embodiment of the invention can be based on a generic model, for example, of a stomach and on this apply the video sequence. However, adaptations may be necessary either by the generic model per se being affected by the picture material or by the picture material being affected by knowledge of the properties of the model. It is, however, important that the virtual instrument acts on the computer model, and not on the video sequence. Since the video sequence contains a certain limited movement in the model such as breathing and beat of the pulse, the underlying model needs to be animated correspondingly so that an operation by way of a virtual instrument hits the same point in the virtual model as the point that can be seen on the video sequence.

In order to visualise changes in the computer model, changes in what is shown need to be made. One way of doing this is to provide a rendered surface of those and only those portions of the model which are affected by the virtual instrument, and to superimpose the rendered surface on the video sequence. Thus, a great advantage compared with known systems and methods is achieved since only those portions that have been changed need to be rendered. This saves computer utility but, above all, the realism is increased for the user as regards the visual impression. Consequently, essentially the entire object is shown to the user as a filmed sequence, which is important on the one hand as regards the user's possibility of recreating the threedimensionality in the two-dimensional picture and, on the other, to increase the feeling of being "for real". Preferably, the video sequence contains a whole breathing and pulse cycle. Since there are more beats of the pulse than breaths during a certain period of time, the video sequence suitably contains a sequence which starts when the beats of the pulse and the breathing take place at the same time and finishes when the beats of the pulse and the breathing occur simultaneously. The reason for this is that the virtual environment should be as similar as possible to the real one.

In addition, an embodiment of the invention allows what is shown of the virtual instruments to be affected by their interaction with the model. Since the video sequence is only a visualisation, while the virtual instruments interact with the model and, thus, uses the information as to depth in the model, information is obtained if the instruments are wholly or partly hidden by protruding parts of the model. For example, a needle is partly hidden as it penetrates the wall of an organ or an instrument may be hidden by an organ that is located in the foreground of the object to be operated on.

Since the virtual instrument works in a three-dimensional virtual environment, it is important to be able to analyse that the user correctly estimates how the three-dimensional environment is built based on the visual impression of the two-dimensional projection. Preferably, the method therefore comprises the step of measuring at least one parameter in the virtual instrument's movements or interaction with the object, the parameter reflecting the user's skill. Parameters which can be measured to estimate the skill are time, number of collisions with tissues, number of incorrect procedures, etc. By following up the simulation in a structured manner, the possibilities of learning are improved, especially learning of procedures that the users have not observed that they made incorrectly at the moment of the simulation.

Furthermore, an embodiment of the invention comprises a method for simulating a surgical operation containing a plurality of surgical procedures on a bodily object, such as an organ, in a virtual environment provided by a computer unit. The environment comprises a three-dimensional mathematically described model of the bodily object, which reflects at least the geometrical and mechanical properties of the bodily object, and a virtual instrument which is controlled by a physical input device connected to the processing unit, which makes it possible to affect the model. The method comprises the steps of representing a two-dimensional projection of the model via a video sequence containing a recorded view of a real bodily object, providing the model in a plurality of states which reflect the object during a number of distinct phases of an operation, providing a first plurality of video sequences which correspond to the natural movements of a real object during the respective states, providing a second plurality of video sequences which each visualise the surgical procedure that shows how the object is changed from one state to another, and of allowing the user to choose between simulating a procedure and looking at a visualisation of the procedure in order to change the object from one state to another.

Consequently, the possibility is achieved of simulating a whole operation. The states which reflect the object during a number of distinct phases of an operation can, for example, consist of an initial state with an unchanged object, an object having an incision for suture or the object with a completed suture. By such a method a training process is provided, in which the continuity in a real procedure is saved by using real picture information. This results in great advantages compared with systems that are based on a solution purely involving video sections, such as the solution which is presented in U.S. Pat. No. 5,791,907 by the users themselves having the possibility in the process of choosing to make the procedures they desire to practice, whereas they can choose to just look at visualisations of the procedures that they already know well or do not handle. Besides, a larger degree of comprehensive understanding is achieved when separate surgical procedures are not simulated individually but put in their context.

Furthermore, an embodiment of the invention comprises a system for simulating a surgical procedure on a bodily object, such as an organ, in a virtual environment provided by a computer unit. The environment comprises a three-dimensional mathematically described model of the bodily object, which reflects at least the geometrical and mechanical properties of the bodily object, and a virtual instrument which is controlled by a physical input device connected to the processing unit, which makes it possible to affect the model. The system comprises a two-dimensional projection of the model, which is represented by a video sequence containing a recorded view of a real bodily object, engagement with the virtual instrument only interacting with the model. This system essentially exhibits the same advantages as the corresponding method mentioned above.

BRIEF DESCRIPTION OF THE DRAWINGS

In the following, an embodiment of the invention will be described in more detail by way of example with reference to the accompanying drawings, in which.

DESCRIPTION OF A PREFERRED EMBODIMENT

Figure 1:
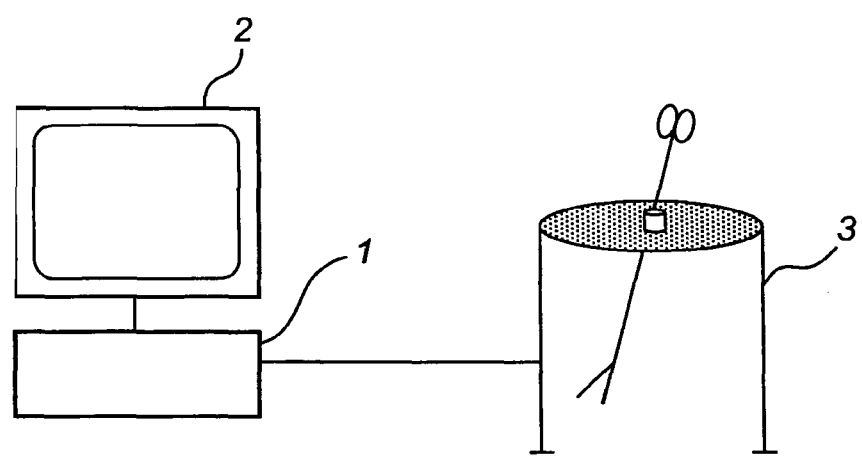
FIG. 1 shows a simulation environment.

A simulation environment according to a preferred embodiment of the invention includes a processing unit 1, a display screen 2, an input device 3, which is shown in FIG. 1. The virtual environment is realised by way of the processing unit 1. The processing unit can, for example, consist of a personal computer which is preferably equipped with a graphics card having 3D-circuits.

Figures 2A, 2B:
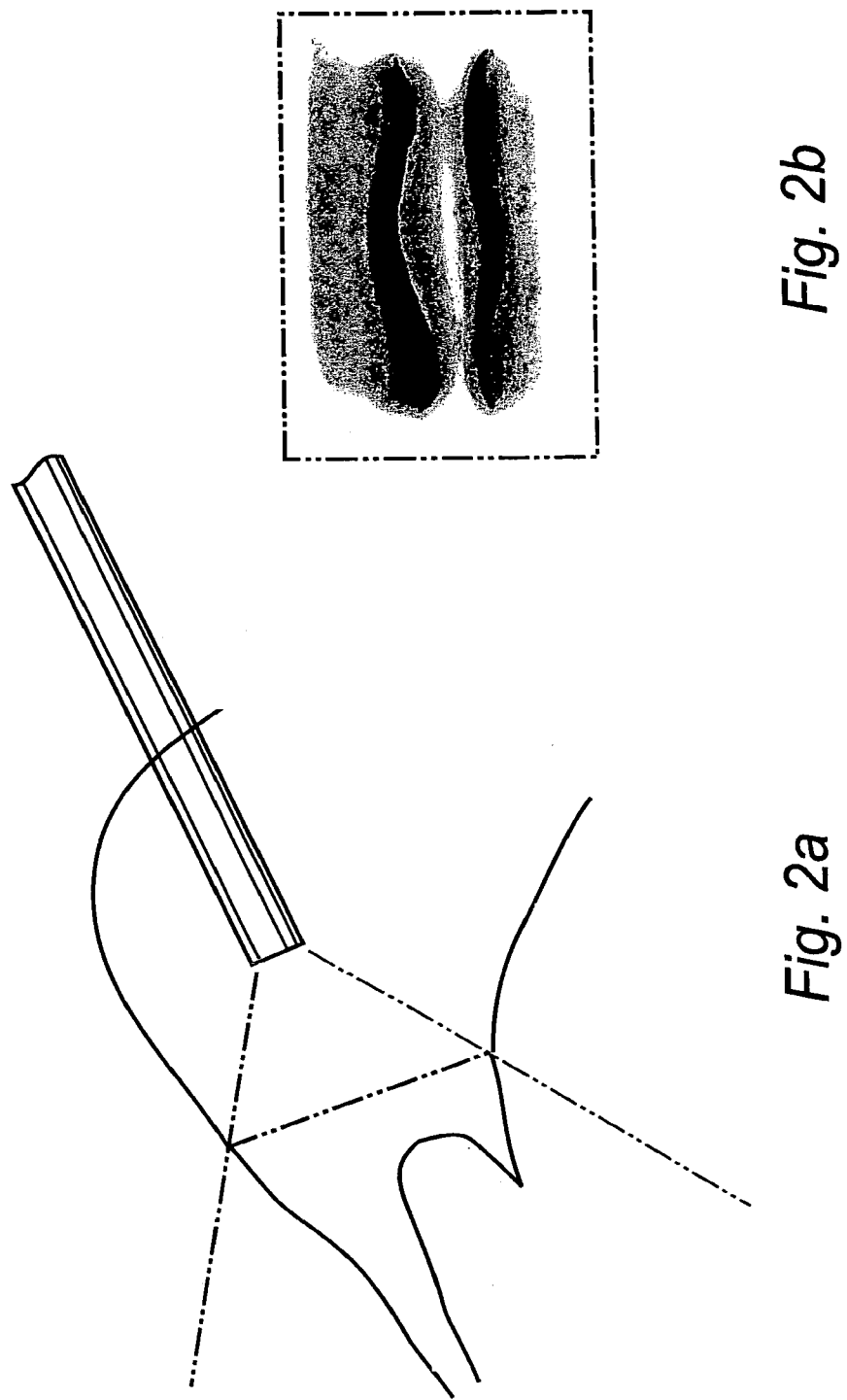
FIGS. 2a-2b show a recording of a video sequence.
Figure 3:
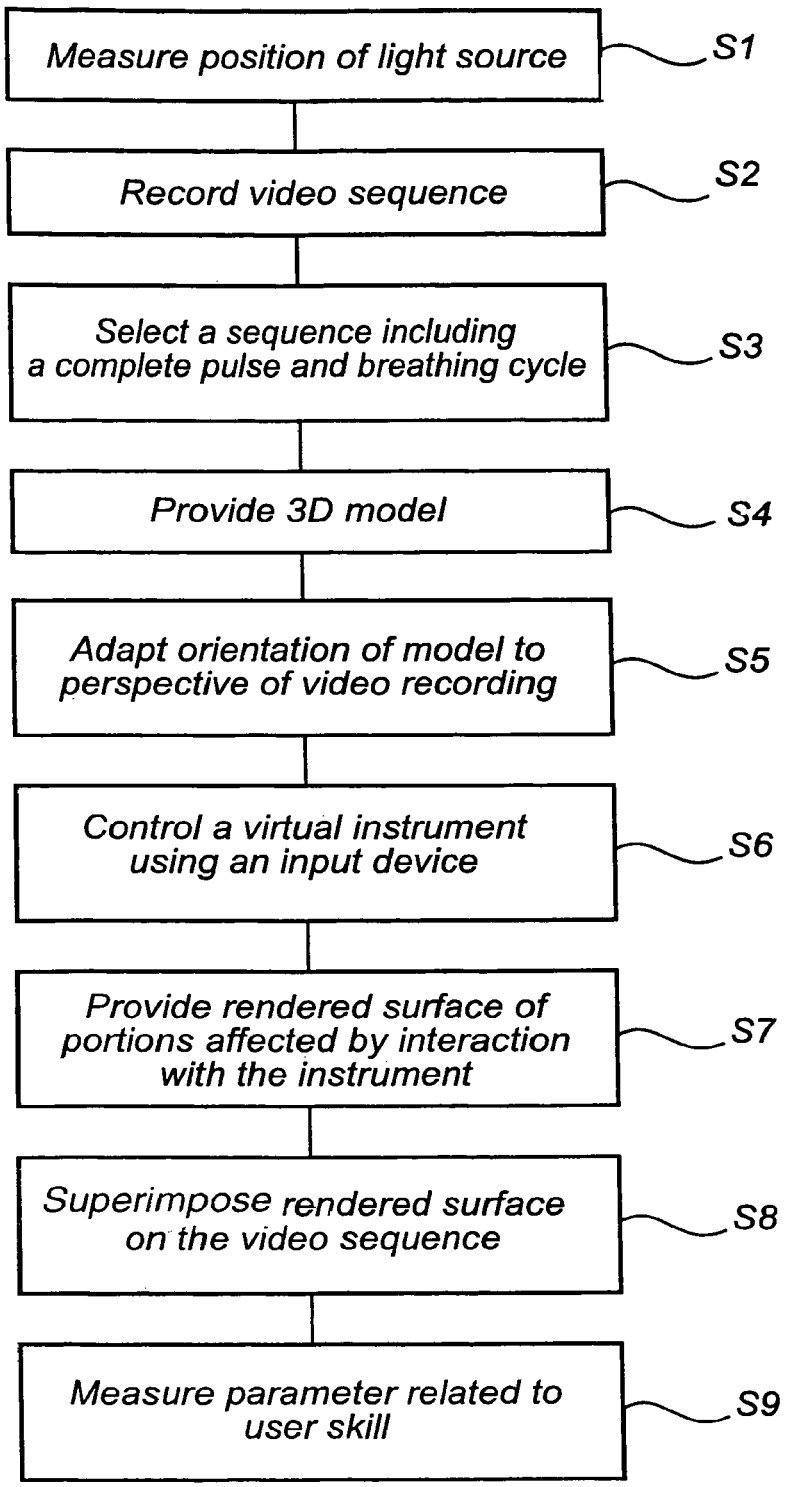
FIG. 3 shows a method for simulating an example embodiment.

FIGS. 2a-2b show how a real surgical procedure is filmed by way of a camera both before, during as well as after the procedure. In order to allow filming inside a body, a laparoscopic camera is used. FIG. 2a shows how a laparoscopic camera is filming inside an organ and the picture obtained is shown in FIG. 2b. Subsequently, this film will constitute the base of the visual properties in the simulation. Apart from the picture information, luminous intensity, light angle and viewing angle are preferably recorded. From this film a section is selected, which constitutes a complete breathing and pulse cycle. Since it has the same beginning and end, it can be placed in a loop in order to continuously reflect the patient's natural movements. This refers to the fact that there is a finite number of filmed pictures which together constitute a filmed video sequence. This video sequence is to be used to show the natural movements of a simulation object which is not affected by the virtual instrument. In addition, the actual operation is recorded, which makes it possible to visualise the whole operation.

In one embodiment a computer model of the objects appearing in the film is then created, which can be an organ, cancer cells, etc., in the virtual environment, based on the visual impression and knowledge of the anatomy of the object. This computer model becomes a three-dimensional model which is drawn relatively freely in a computer environment. In another embodiment a number of generic models of human organs and other objects have already been created. Irrespective of the point of departure, it is on this model that the simulation will be based. It is thus important that the model has the geometrical, mechanical and tactile properties that a real object or organ has. Consequently, the model can be described entirely mathematically. The mathematically described data structure contains information about both surface and volume. The surface information can be used with the purpose of rendering and the volume information is necessary in order to learn about the mechanical and visual properties of the inside of the object. Examples of data structures are voxels or octtrees.

It is important to obtain the same perspective of the modelled object as the filmed object. In the simplest embodiment, this is carried out by turning the model in a computer environment in order to optically determine when the correct perspective is found. In a more advanced embodiment there are algorithms which turn and/or scale the model until it corresponds to the filmed object. During the comparison, one or more pictures from the filmed sequence are used. One way of comparing pictures from the film and projections of the model is to start with a picture from the film and then proceed with more pictures from the film with the purpose of possibly compensating by turning the model somewhat. Another way of comparing a picture from the film with a specific perspective of the model is to compare sharp lines in the picture with the outlines of the model in the projection. In the same way, it is possible to determine if darker portions in the picture together with information about the location of the light source are positioned deeper down than another portion. These comparisons result in a given perspective being obtained, which is then locked to be determined as the same as that from which the real object is filmed.

For the user of the simulation equipment, the limited video sequence is now presented as a projection of the model. Thus, a completely realistic environment for practicing is achieved. Since the model is located behind the film and the virtual instruments really operate in the model, full realism is achieved considering that the depth effect is fetched from the model and not the film. The film is presented to the user on the display screen 2.

The model and its visualisation through the video sequence now constitute the basis for the actual interaction with the user. In order to resemble a real situation, a input device 3 is used, which essentially is identical to that used in a real operation. However, this is mounted in a stand and connected to sensors for detecting movements. As in a real operation, the user looks at the movements of the instruments on the same screen 2 as that on which the visualisation of the model is shown. The instruments are represented as they would have looked like if they engaged with a real body. The difference is that the visualisation on the screen 2 does not originate from a laparoscopic camera, but from a visualisation created in the processing unit. The virtual instruments thus engage with the model, which allows feedback of power when the model contains the necessary data. Naturally, when real instruments engage with a real object, a change of the object occurs; for instance, an incision with a knife results in an incision in the object. Consequently, this is shown in a real operation on the screen which shows what the camera is filming. In the preferred embodiment rendered portions are created of the areas in the model which have changed visually in the perspective shown to the user. These are then superimposed on the video sequence. In order to make the rendered portions reflect the natural movements of the object, just as many rendered portions must be created as there are pictures in the video sequence.

In order to create a realistic environment, there is also in the preferred embodiment a device for affecting how the virtual instruments 3 are visualised on the screen 2. Since the virtual object is completely described in three dimensions at each moment of the animated computer model, it is possible to determine when a collision between the virtual instrument and the virtual object takes place. In reality, a deformation of the object occurs which is highly evident, for example, when the tip of a needle is about to penetrate the tissue. The same effect is achieved by finding the point where the instrument hits the object and determining deformations. Subsequently, a new surface structure is determined in the deformed area and from information about the light source when filming the video sequence, a new picture can be created. This picture is placed on the film in a new layer and by using the transparency in the borders which can be obtained by way of special 3D-graphics cards, the superposition can take place with an extremely small visual border. By knowledge of the surfaces of the objects and the conditions in depth in the picture, the visualisation of the virtual instruments can be affected. Thus, the processing unit may know which parts of the virtual instruments have been covered by parts of the objects that are located in front of the instrument or the parts that are covered if the instrument has penetrated in an object.

Advantageously, a form of lesson comprising a complete surgical procedure or operation can also be simulated. This is based on a number of procedures being prepared either for simulation or visualisation. When visualising, the video recordings are thus used which have been mentioned at the beginning of this section which shows a real filmed operation.

It should be understood that a number of modifications of the embodiment described above are possible within the scope of the invention; for example rendered portions of changes of the surface structure of the model can be placed in several layers on the video sequence. Such variants and similar variants must be considered comprised by the invention as defined by the appended claims.

The invention claimed is:

1. A method for simulating a surgical procedure on a tangible, corporeal bodily object in a virtual environment provided by a processing unit, the virtual environment including
   a three-dimensional mathematically described model of the tangible, corporeal bodily object, which at least reflects the geometrical and mechanical properties of the tangible, corporeal bodily object, and
   a virtual instrument configured to interact with the three-dimensional, model the method comprising the steps of:
   receiving user input from an input device connected to said processing unit,
   controlling said virtual instrument and interactions of said virtual instrument with said model based on said user input,
   providing a pre-recorded video sequence of a tangible, corporeal bodily object being subjected to a surgical procedure,
   determining a perspective in which at least a portion of said pre-recorded video sequence is recorded and determining a two-dimensional projection of said model corresponding to the perspective in which said pre-recorded video sequence is recorded,
   displaying on a screen said pre-recorded video sequence which visually represents said two-dimensional projection,
   providing a rendered surface to simulate a surgical procedure, the rendered surface being only portions of said three-dimensional model which are affected by said virtual instrument,
   superimposing said rendered surface on said pre-recorded video sequence of a surgical procedure,
   during interaction between the virtual instrument and the three-dimensional model, determining which parts of the virtual instrument that are at least partly covered by protruding parts of the three-dimensional model, and
   displaying on said screen only parts of the virtual instrument that are not covered by said three-dimensional model,
   wherein the three-dimensional mathematically described model of the tangible, corporeal bodily object, further reflects the tactile properties of the tangible, corporeal bodily object.

2. A method for simulating a surgical procedure on a tangible, corporeal bodily object in a virtual environment provided by a processing unit, the virtual environment including
   a three-dimensional mathematically described model of the tangible, corporeal bodily object, which at least reflects the geometrical and mechanical properties of the tangible, corporeal bodily object, and
   a virtual instrument configured to interact with the three-dimensional, model the method comprising the steps of:
   receiving user input from an input device connected to said processing unit,
   controlling said virtual instrument and interactions of said virtual instrument with said model based on said user input,
   providing a pre-recorded video sequence of a tangible, corporeal bodily object being subjected to a surgical procedure,
   determining a perspective in which at least a portion of said pre-recorded video sequence is recorded and determining a two-dimensional projection of said model corresponding to the perspective in which said pre-recorded video sequence is recorded,
   displaying on a screen said pre-recorded video sequence which visually represents said two-dimensional projection,
   providing a rendered surface to simulate a surgical procedure, the rendered surface being only portions of said three-dimensional model which are affected by said virtual instrument,
   superimposing said rendered surface on said pre-recorded video sequence of a surgical procedure,
   during interaction between the virtual instrument and the three-dimensional model, determining which parts of the virtual instrument that are at least partly covered by protruding parts of the three-dimensional model, and
   displaying on said screen only parts of the virtual instrument that are not covered by said three-dimensional model,
   wherein the superimposing further includes providing the rendered surface on said pre-recorded video sequence to simultaneously visualize changes in the three-dimensional model corresponding to physiological changes to the corporeal bodily object occurring in the video sequence.

3. A system for simulating a surgical procedure on a tangible, corporeal bodily object, comprising:
   a processing unit configured to provide a virtual environment including a three-dimensional mathematically described model of said tangible, corporeal bodily object, the three-dimensional model reflecting the geometrical and mechanical properties of said tangible, corporeal bodily object,
   a virtual instrument configured to interact with said three-dimensional model,
   a physical input device connected to said processing unit, said physical input device being configured to provide input for controlling said virtual instrument, and
   a pre-recorded video sequence of a tangible, corporeal bodily object being subjected to a surgical procedure, wherein
   said processing unit being configured to:
   determine a perspective in which at least a portion of said pre-recorded video sequence is recorded and determine a two-dimensional projection of said model corresponding to the perspective in which said pre-recorded video sequence has been recorded, display on a screen at least a portion of said pre-recorded video sequence which visually represents said two-dimensional projection,
provide a rendered surface to simulate a surgical procedure, the rendered surface being only of portions of said three-dimensional model which are affected by said virtual instrument,
superimpose said rendered surface on said pre-recorded video sequence of a surgical procedure,
during interaction between the virtual instrument and the three-dimensional model, determine which parts of the virtual instrument that are at least partly covered by protruding parts of the three-dimensional model, and
display on said screen only parts of the virtual instrument that are not covered by said three-dimensional model
wherein the three-dimensional mathematically described model of the tangible, corporeal bodily object, further reflects the tactile properties of the tangible, corporeal bodily object.

4. A system for simulating a surgical procedure on a tangible, corporeal bodily object, comprising:
a processing unit configured to provide a virtual environment including a three-dimensional mathematically described model of said tangible, corporeal bodily object, the three-dimensional model reflecting the geometrical and mechanical properties of said tangible, corporeal bodily object,
a virtual instrument configured to interact with said three-dimensional model,
a physical input device connected to said processing unit, said physical input device being configured to provide input for controlling said virtual instrument, and
a pre-recorded video sequence of a tangible, corporeal bodily object being subjected to a surgical procedure, wherein
said processing unit being configured to:
determine a perspective in which at least a portion of said pre-recorded video sequence is recorded and determine a two-dimensional projection of said model corresponding to the perspective in which said pre-recorded video sequence has been recorded,
display on a screen at least a portion of said pre-recorded video sequence which visually represents said two-dimensional projection,
provide a rendered surface to simulate a surgical procedure, the rendered surface being only of portions of said three-dimensional model which are affected by said virtual instrument,
superimpose said rendered surface on said pre-recorded video sequence of a surgical procedure,
during interaction between the virtual instrument and the three-dimensional model, determine which parts of the virtual instrument that are at least partly covered by protruding parts of the three-dimensional model, and
display on said screen only parts of the virtual instrument that are not covered by said three-dimensional model
wherein the processing unit is further configured to superimpose said rendered surface on said pre-recorded video sequence to simultaneously visualize changes in the three-dimensional model corresponding to physiological changes to the corporeal bodily object occurring in the video sequence.

* * * * *